(12) United States Patent
Stahmann et al.

(10) Patent No.: US 7,142,914 B2
(45) Date of Patent: Nov. 28, 2006

(54) MODE TRANSITION TIMING FOR SYNCHRONIZED PACING

(75) Inventors: Jeffrey E. Stahmann, Ramsey, MN (US); Rene H. Wentkowski, White Bear Lake, MN (US); James Kalgren, Lino Lakes, MN (US); Sylvia Quiles, Coon Rapids, MN (US); Scott Vanderlinde, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 691 days.

(21) Appl. No.: 10/222,130

(22) Filed: Aug. 16, 2002

(65) Prior Publication Data

US 2003/0004550 A1 Jan. 2, 2003

Related U.S. Application Data

(63) Continuation of application No. 09/748,797, filed on Dec. 26, 2000, now Pat. No. 6,438,421.

(51) Int. Cl.
*A61N 1/05* (2006.01)

(52) U.S. Cl. .......................................................... 607/9

(58) Field of Classification Search ................ 607/4–30
See application file for complete search history.

(56) References Cited

U.S. PATENT DOCUMENTS

| | | | |
|---|---|---|---|
| 4,354,497 A | 10/1982 | Kahn | 128/419 D |
| 4,928,688 A | 5/1990 | Mower | 128/419 PG |
| 5,156,149 A | 10/1992 | Hudrlik | 128/419 PG |
| 5,174,289 A | 12/1992 | Cohen | 128/419 PG |
| 5,233,985 A | 8/1993 | Hudrlik | 607/27 |
| 5,267,560 A | 12/1993 | Cohen | 607/25 |
| 5,370,665 A | 12/1994 | Hudrlik | 607/9 |
| 5,514,161 A | 5/1996 | Limousin | 607/9 |
| 5,584,867 A | 12/1996 | Limousin et al. | 607/9 |
| 5,674,259 A | 10/1997 | Gray | 607/20 |
| 5,797,970 A | 8/1998 | Pouvreau | 607/9 |
| 5,935,160 A | 8/1999 | Auricchio et al. | 607/122 |
| RE38,119 E | 5/2003 | Mower | 607/9 |
| 2005/0021099 A1 | 1/2005 | Stahmann et al. | |

OTHER PUBLICATIONS

U.S. Patent Office Patent Application Information Retrieval (PAIR) search results for U.S. Appl. No. 10/214,474, filed on Aug. 8, 2002, entitled "Method and Apparatus for Treating Hemodynamic Disfunction", 3 pgs.
Guidant, "Contak TR CHFD Model 1241"*System Guide*, Congestive Heart Failure Device, (1999), 1–191.
Medtronic, "Insync III Device Model 8042", *Device Programming Guide*, Insync III Device Model 8042, Vision Programmer Software Model 9981, (2002), 1–260.
Medtronic, "Insync III Device Model 8042", *Device Reference Guide*, Insync III Device Model 8042, Vision Programmer Software Model 9981, (2002), 1–252.
St. Jude Medical, "Atlas + HF Models V–343, V–341", *User's Manual*, Implantable Cardioverter–Defribrillator, (Sep. 2003), 1–30.
St. Jude Medical, "Epic HF Model V–339", *User's Manual*, Implantable Cardioverter–Defribrillator, (Jul. 2002), 1–26.
St. Jude Medical, "Model 3510 Programmer with Model 3307 Software", *Reference Manual*, For Atlas, Atlas+, Epic, Epic+, Photon u and Photon Implantable Cardioverter/Defribrillators, (Sep. 2003), 1–314.

*Primary Examiner*—Scott M. Getzow
(74) *Attorney, Agent, or Firm*—Schwegman, Lundberg, Woessner & Kluth, P.A.

(57) ABSTRACT

A system and method for avoiding short-interval paces during pacing mode transitions. The method may be particularly useful in switching to or from a biventricular pacing mode.

20 Claims, 3 Drawing Sheets

MODE TRANSITION TIMING FOR SYNCHRONIZED PACING

CROSS-REFERENCE TO RELATED APPLICATION(S)

This patent application is a continuation of U.S. patent application Ser. No. 09/748,797, filed on Dec. 26, 2000, now issued as U.S. Pat. No. 6,438,421, the specification of which is incorporated by reference herein.

FIELD OF THE INVENTION

This invention pertains to methods and apparatus for cardiac rhythm management. In particular, the invention relates to methods and apparatus for providing ventricular resynchronization therapy.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. (As the term is used herein, a pacemaker is any cardiac rhythm management device with a pacing functionality regardless of any other functions it may perform such as cardioversion or defibrillation.)

The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate.

Pacing therapy can also be used in the treatment of congestive heart failure (CHF), which is a clinical syndrome in which an abnormality of cardiac function causes cardiac output to fall below a level adequate to meet metabolic demand. CHF can be due to a variety of etiologies with that due to ischemic heart disease being the most common. Some CHF patients suffer from some degree of AV block or are chronotropically deficient such that their cardiac output can be improved with conventional bradycardia pacing. It has also been shown, however, that some CHF patients suffer from intraventricular and/or interventricular conduction defects (e.g., bundle branch blocks) such that their cardiac outputs can be increased by improving the synchronization of right and left ventricular contractions with electrical stimulation. Cardiac rhythm management devices have therefore been developed which provide electrical stimulation to one or both ventricles in an attempt to improve the coordination of ventricular contractions, termed ventricular resynchronization therapy. Such electrical stimulation will be referred to herein as "pacing" even if the stimulation is not delivered so as to enforce a particular heart rate.

SUMMARY OF THE INVENTION

Cardiac resynchronization pacing modes involve the delivery of paces to a pacing site based upon events occurring at another site. In such modes, one chamber is designated the rate chamber or rate site, and one or more pacing sites in the same or contralateral chamber are designated synchronized sites. The synchronized sites are paced upon expiration of escape intervals which are reset by senses or paces occurring at the rate site. The present invention is concerned with the effect of transitions between pacing modes in which a pacing site is paced at different pacing instants with respect to expiration of a programmed escape interval that is reset by a sense or pace from another site. During the cardiac cycle in which the pacing mode transition takes place, a synchronized site may receive a pace at an abnormally short pacing interval if it is paced at an earlier pacing instant with respect to the escape interval expiration in the mode that is switched to, where a pacing interval is the time between successive paces delivered to the site in the absence of intrinsic activity. This is because the pacing mode itself does not directly control the interval at which a pace occurs until after the transition is completed. Such a shortened pacing interval may have adverse consequences. In accordance with the present invention, if a pacing interval for a pacing site would be below a specified minimum pacing interval value during a pacing mode transition, the pace may be inhibited or the pacing interval lengthened for the cardiac cycle in which the transition takes place.

Exemplary embodiments of the invention are applied to situations where the left or both ventricles are paced upon expiration of escape intervals reset by right ventricular senses or paces, and where there is a transition to or from a biventricular pacing mode with a ventricular offset interval. In those situations, the left ventricle is paced in accordance with a first pacing mode such that a pace is delivered at a specified pacing instant defined with respect to expiration of a ventricular escape interval, and a transition is made to a second pacing mode in which the left ventricle is paced at an earlier specified pacing instant defined with respect to expiration of a ventricular escape interval than in the first pacing mode. In accordance with the invention, a left ventricular pace is delayed during the cardiac cycle in which the transition occurs if the left ventricular pacing instant occurs at an interval less than a specified minimum pacing interval. In another embodiment, the pace is inhibited for that cardiac cycle if the pacing interval would be below the specified minimum value.

DESCRIPTION OF THE INVENTION

As is described more fully below, a pacing mode defines how pacing pulses are delivered to the heart by a pacemaker in response to sensed events and expiration of specified time intervals, the latter sometimes referred to as escape intervals. Certain pacing modes that pace multiple sites, such as resynchronization pacing, may define different pacing instants for different pacing sites with respect to the expiration of an escape interval. A pacemaker may be capable of operating in a number of different pacing modes and be capable of transitioning between modes either upon command from an external programmer or automatically under certain circumstances. When transitioning to or from such a pacing mode, a pacing site may be paced at a shorter interval than would otherwise be allowed by the pacemaker. This may have the effect of triggering the fault-protection circuitry in the pacemaker which is designed to protect against overpacing. There is also the risk that pacing a ventricle at an abnormally short pacing interval may induce an arrhythmia. The present invention is directed toward providing a system and method for dealing with this problem.

1. Hardware Platform

Pacemakers are typically implanted subcutaneously or submuscularly in a patient's chest and have leads threaded intravenously into the heart to connect the device to electrodes used for sensing and pacing. Leads may also be positioned on the epicardium by various means. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
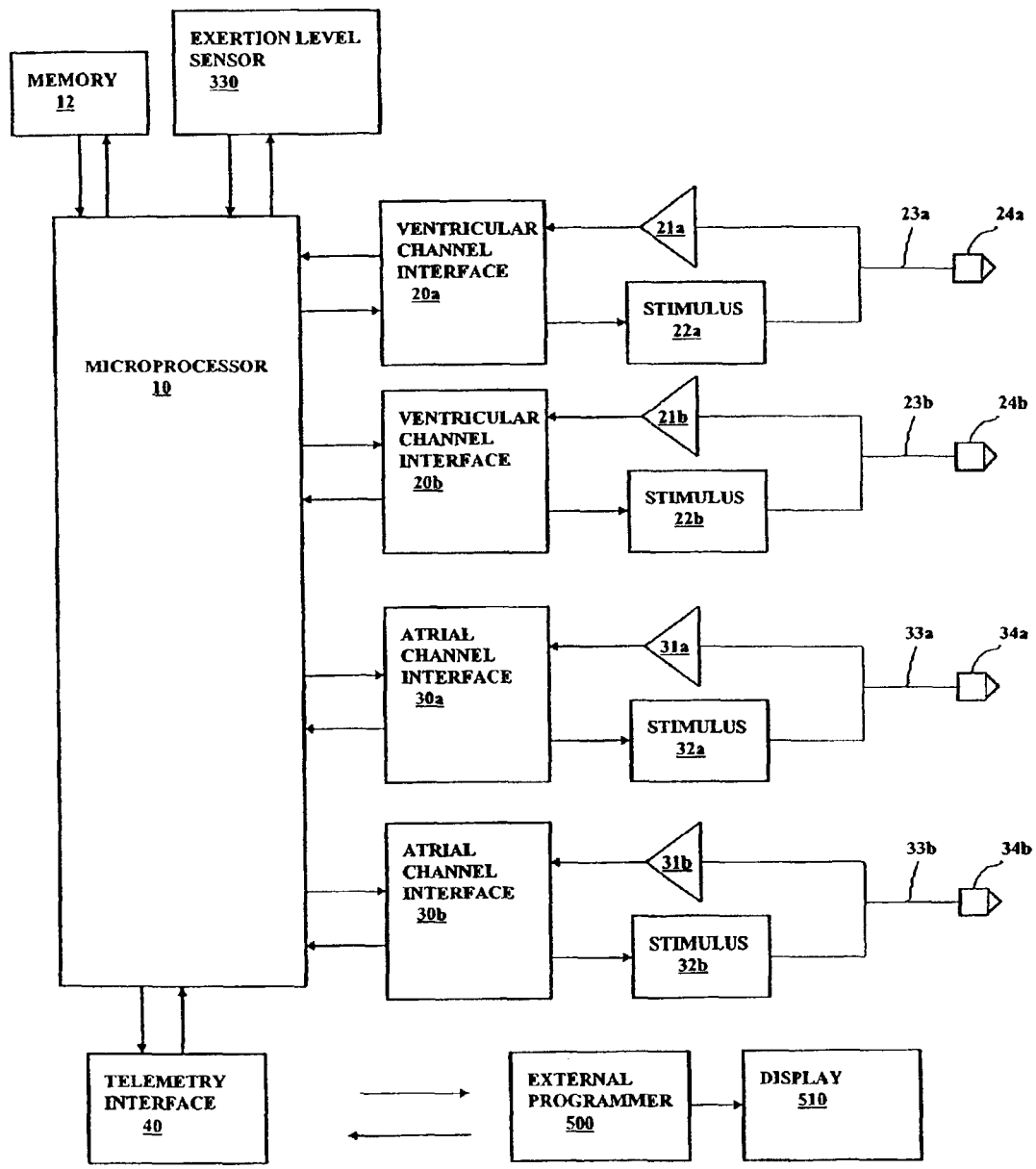
FIG. 1 is a system diagram of a pacemaker configured for biventricular pacing and sensing.

FIG. 1 shows a system diagram of a microprocessor-based pacemaker physically configured with sensing and pacing channels for both atria and both ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The pacemaker has atrial sensing and pacing channels comprising electrodes 34*a–b*, leads 33*a–b*, sensing amplifiers 31*a–b*, pulse generators 32*a–b*, and atrial channel interfaces 30*a–b* which communicate bidirectionally with microprocessor 10. The device also has ventricular sensing and pacing channels for both ventricles comprising electrodes 24*a–b*, leads 23*a–b*, sensing amplifiers 21*a–b*, pulse generators 22*a–b*, and ventricular channel interfaces 20*a–b*. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads which include two electrodes for outputting a pacing pulse and/or sensing intrinsic activity. The channel interfaces 20*a–b* and 30*a–b* include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 which has an associated display 510. A pacemaker incorporating the present invention may possess all of the components in FIG. 1 and be programmable so as to operate in a number of different modes, or it may have only those components necessary to operate in a particular mode.

The controller 10 controls the overall operation of the device in accordance with programmed instructions stored in memory. The controller 10 interprets sense signals from the sensing channels and controls the delivery of paces in accordance with a pacing mode. The sensing circuitry of the pacemaker generates atrial and ventricular sense signals when voltages sensed by the electrodes exceed a specified threshold. The sense signals from each channel, together with the paces delivered, represent an electrogram that can either be transmitted via the telemetry link to an external programmer or stored for later transmission. The operation of the pacemaker and the patient's cardiac activity may thus be observed in real-time or over a selected historical period. In the latter case, the recording of an electrogram may be triggered by the detection of certain events or conditions such as an arrhythmia.

2. Bradycardia Pacing Modes

Bradycardia pacing modes refer to pacing algorithms used to pace the atria and/or ventricles when the intrinsic atrial and/or ventricular rate is inadequate due to, for example, AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modern pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

Another type of synchronous pacing is atrial-triggered or ventricular-triggered pacing. In this mode, an atrium or ventricle is paced immediately after an intrinsic beat is detected in the respective chamber. Triggered pacing of a heart chamber is normally combined with inhibited demand pacing so that a pace is also delivered upon expiration of an escape interval in which no intrinsic beat occurs. Such triggered pacing may be employed as a safer alternative to asynchronous pacing when, due to far-field sensing of electromagnetic interference from external sources or skeletal muscle, false inhibition of pacing pulses is a problem. If a sense in the chamber's sensing channel is an actual depolarization and not a far-field sense, the triggered pace is delivered during the chamber's physiological refractory period and is of no consequence.

Finally, rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which atrial tracking modes cannot be used. In a rate-adaptive pacemaker operating in a ventricular pacing mode, for example, the LRL is adjusted in accordance with exertion level measurements such as from an accelerometer or minute ventilation sensor in order for the heart rate to more nearly match metabolic demand. The adjusted LRL is then termed the sensor-indicated rate.

3. Cardiac Resynchronization Therapy

Cardiac resynchronization therapy is pacing stimulation applied to one or more heart chambers in a manner that restores or maintains synchronized bilateral contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. In that sense, conventional bradycardia pacing of an atrium and/or a ventricle may be considered as resynchronization therapy. Resynchronization pacing, however, may also involve pacing both ventricles and/or both atria in accordance with a synchronized pacing mode as described below. A single chamber may also be resynchronized to compensate for intra-atrial or intra-ventricular conduction delays by delivering paces to multiple sites of the chamber.

It is advantageous to deliver resynchronization therapy in conjunction with one or more synchronous bradycardia pacing modes, such as are described above. One atrium and/or one ventricle are designated as rate chambers, and paces are delivered to the rate chambers based upon pacing and sensed intrinsic activity in the chamber in accordance with the bradycardia pacing mode. In a single-chamber bradycardia pacing mode, for example, one of the paired atria or one of the ventricles is designated as the rate chamber. In a dual-chamber bradycardia pacing mode, either the right or left atrium is selected as the atrial rate chamber and either the right or left ventricle is selected as the ventricular rate chamber. The heart rate and the escape intervals for the pacing mode are defined by intervals between sensed and paced events in the rate chambers only. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. In bilateral synchronized pacing, which may be either biatrial or biventricular synchronized pacing, the heart chamber contralateral to the rate chamber is designated as a synchronized chamber. For example, the right ventricle may be designated as the rate ventricle and the left ventricle designated as the synchronized ventricle, and the paired atria may be similarly designated. Each synchronized chamber is then paced in a timed relation to a pace or sense occurring in the contralateral rate chamber in accordance with a synchronized pacing mode as described below.

One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. One example of such pacing is biventricular offset synchronized pacing where both ventricles are paced with a specified offset interval. The rate ventricle is paced in accordance with a synchronous bradycardia mode which may include atrial tracking, and the ventricular escape interval is reset with either a pace or a sense in the rate ventricle. (Resetting in this context refers to restarting the interval in the case of an LRL ventricular escape interval and to stopping the interval in the case of an AVI.) Thus, a pair of ventricular paces are delivered after expiration of the AVI escape interval or expiration of the LRL escape interval, with ventricular pacing inhibited by a sense in the rate ventricle that restarts the LRL escape interval and stops the AVI escape interval. In this mode, the pumping efficiency of the heart will be increased in some patients by simultaneous pacing of the ventricles with an offset of zero. However, it may be desirable in certain patients to pace one ventricle before the other in order to compensate for different conduction velocities in the two ventricles, and this may be accomplished by specifying a particular positive or negative ventricular offset interval.

Another synchronized mode is triggered synchronized pacing. In one type of triggered synchronized pacing, the synchronized chamber is paced after a specified trigger interval following a sense in the rate chamber, while in another type the rate chamber is paced after a specified trigger interval following a sense in the synchronized chamber. The two types may also be employed simultaneously. For example, with a trigger interval of zero, pacing of one chamber is triggered to occur in the shortest time possible after a sense in the other chamber in order to produce a coordinated contraction. (The shortest possible time for the triggered pace is limited by a sense-to-pace latency period dictated by the hardware.) This mode of pacing may be desirable when the intra-chamber conduction time is long enough that the pacemaker is able to reliably insert a pace before depolarization from one chamber reaches the other. Triggered synchronized pacing can also be combined with offset synchronized pacing such that both chambers are paced with the specified offset interval if no intrinsic activity is sensed in the rate chamber and a pace to the rate chamber is not otherwise delivered as a result of a triggering event. A specific example of this mode is ventricular triggered synchronized pacing where the rate and synchronized chambers are the right and left ventricles, respectively, and a sense in the right ventricle triggers a pace to the left ventricle and/or a sense in the left ventricle triggers a pace to the right ventricle.

As with other synchronized pacing modes, the rate chamber in a triggered synchronized pacing mode can be paced with one or more synchronous bradycardia pacing modes. If the rate chamber is controlled by a triggered bradycardia mode, a sense in the rate chamber sensing channel, in addition to triggering a pace to the synchronized chamber, also triggers an immediate rate chamber pace and resets any rate chamber escape interval. The advantage of this modal combination is that the sensed event in the rate chamber sensing channel might actually be a far-field sense from the synchronized chamber, in which case the rate chamber pace should not be inhibited. In a specific example, the right and left ventricles are the rate and synchronized chambers, respectively, and a sense in the right ventricle triggers a pace to the left ventricle. If right ventricular triggered pacing is also employed as a bradycardia mode, both ventricles are paced after a right ventricular sense has been received to allow for the possibility that the right ventricular sense was actually a farfield sense of left ventricular depolarization in the right ventricular channel. If the right ventricular sense were actually from the right ventricle, the right ventricular pace would occur during the right ventricle's physiological refractory period and cause no harm.

As mentioned above, certain patients may experience some cardiac resynchronization from the pacing of only one ventricle and/or one atrium with a conventional bradycardia pacing mode. It may be desirable, however, to pace a single atrium or ventricle in accordance with a pacing mode based upon senses from the contralateral chamber. This mode, termed synchronized chamber-only pacing, involves pacing only the synchronized chamber based upon senses from the rate chamber. An example of synchronized chamber-only pacing is left ventricle-only synchronized pacing where the rate and synchronized chambers are the right and left ventricles, respectively. Left ventricle-only synchronized pacing may be advantageous where the conduction velocities within the ventricles are such that pacing only the left ventricle results in a more coordinated contraction by the ventricles than with conventional right ventricular pacing or biventricular pacing. Left ventricle-only synchronized pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval and stops the AVI escape interval.

In the synchronized modes described above, the rate chamber is synchronously paced with a mode based upon detected intrinsic activity in the rate chamber, thus protecting the rate chamber against paces being delivered during the vulnerable period. In order to provide similar protection to the synchronized chamber, a synchronized chamber protection period (SCPP) may be provided. The SCPP is a programmed interval which is initiated by sense or pace occurring in the synchronized chamber during which paces to the synchronized chamber are inhibited. For example, if the right ventricle is the rate chamber and the left ventricle is the synchronized chamber, a left ventricular protection period LVPP is triggered by a left ventricular sense which inhibits a left ventricular pace which would otherwise occur before the escape interval expires. The SCPP may be adjusted dynamically as a function of heart rate and may be different depending upon whether it was initiated by a sense or a pace. The SCPP provides a means to inhibit pacing of the synchronized chamber when a pace might be delivered during the vulnerable period or when it might compromise pumping efficiency by pacing the chamber too close to an intrinsic beat. In the case of a triggered mode where a synchronized chamber sense triggers a pace to the synchronized chamber, the pacing mode may be programmed to ignore the SCPP during the triggered pace. Alternatively, the mode may be programmed such that the SCPP starts only after a specified delay from the triggering event, which allows triggered pacing but prevents pacing during the vulnerable period.

In the case of synchronized chamber-only synchronized pacing, a synchronized chamber pace may be inhibited if a synchronized chamber sense occurs within a protection period prior to expiration of the rate chamber escape interval. Since the synchronized chamber pace is inhibited by the protection period, the rate chamber is not pseudo-paced and, if no intrinsic activity is sensed in the rate chamber, it will be paced upon expiration of the rate chamber escape intervals. The rate chamber pace in this situation may thus be termed a safety pace. For example, in left ventricle-only synchronized pacing, a right ventricular safety pace is delivered if the left ventricular pace is inhibited by the left ventricular protection period and no right ventricular sense has occurred.

Synchronized pacing may be applied to multiple sites of a single chamber. In these synchronized modes, one sensing/pacing channel is designated as the rate channel for sensing/pacing a rate site, and the other sensing/pacing channels in either the same or the contralateral chamber are designated as synchronized channels for sensing one or more synchronized sites. Pacing and sensing in the rate channel follows rate chamber timing rules, while pacing and sensing in the synchronized channels follows synchronized chamber timing rules as described above. The same or different synchronized pacing modes may be used in each synchronized channel.

4. Mode Transition Timing

In inhibited demand pacing modes, paces are always delivered upon expiration of an escape interval. When a ventricle is paced upon expiration of an escape interval that is restarted by a sense or pace in that ventricle, for example, the pacing instant for the ventricle is necessarily at the same time that the escape interval expires. Certain pacing modes, however, particularly those used for cardiac resynchronization, involve pacing a synchronized site at a pacing instant defined with respect to expiration of an escape interval that is reset by an event occurring at another site. In these modes, the pacing instant for a pacing site does not necessarily coincide with the time that the escape interval expires.

For example, in biventricular pacing based upon right ventricular events, the ventricular escape interval is reset by a right ventricular sense or pace. The right ventricle in this mode is always paced upon expiration of the escape interval, but the pace for the left ventricle may either precede or follow the right ventricular pace in accordance with the specified biventricular offset interval. When transitioning to a pacing mode in which the pacing instant for the left ventricle occurs earlier with respect to the escape interval expiration than in the previous pacing mode, the left ventricle will be paced at a pacing interval shorter than the programmed escape interval during the cardiac cycle that the transition takes place, where the pacing interval is the time between successive left ventricular paces in the absence of intrinsic activity. This may occur, for example, when a pacemaker switches to or from a biventricular pacing mode in which paces to the two ventricles are separated by an offset interval. The examples that follow will deal with this specific situation.

Figure 2:
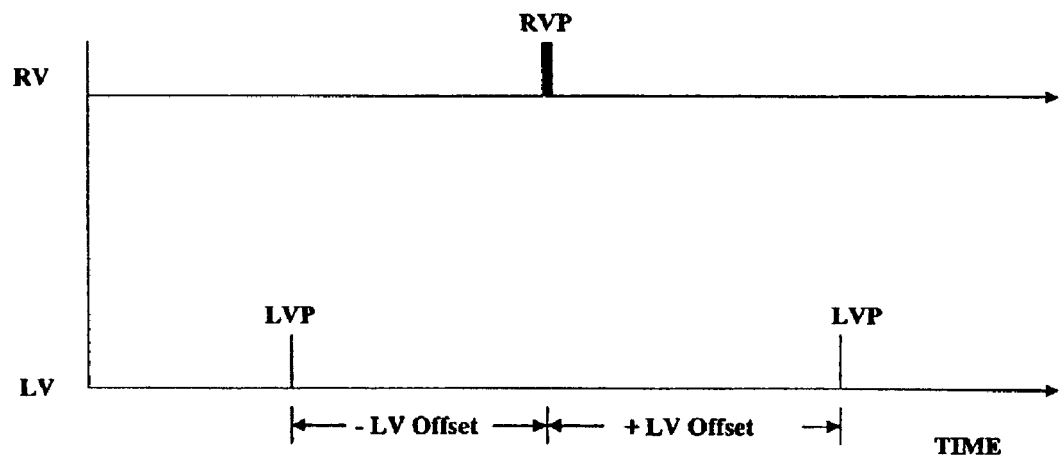
FIG. 2 illustrates a biventricular synchronized pacing mode.

FIG. 2 is a diagram of right and left pacing channels labeled RV and LV that shows how the pacing instants for the left ventricle and right ventricle may differ in a biventricular pacing mode based upon right ventricular events. The right ventricular pace RVP is delivered upon expiration of a ventricular escape interval. The left ventricular pace LVP may be delivered coincident with the right ventricular pace or may occur before or after the right ventricular pace as specified by a negative or positive ventricular offset interval, respectively.

Figure 3A:
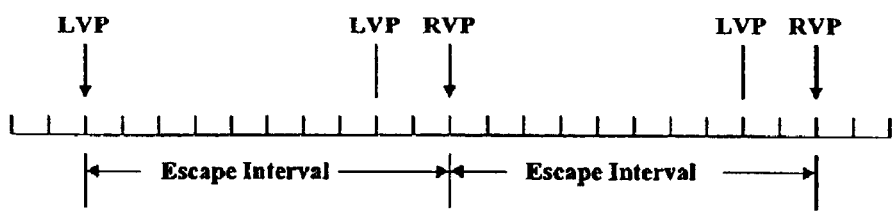
FIGS. 3A through 3E show examples of pacing timing diagrams during mode transitions.
Figure 3B:
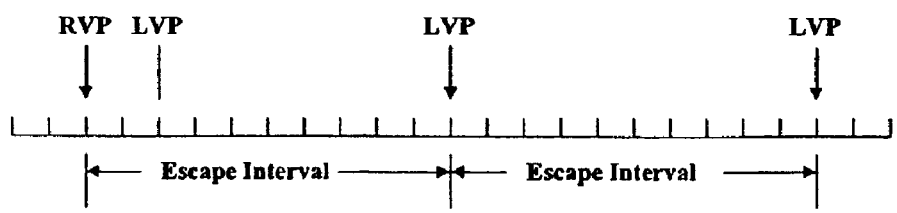
Figure 3C:
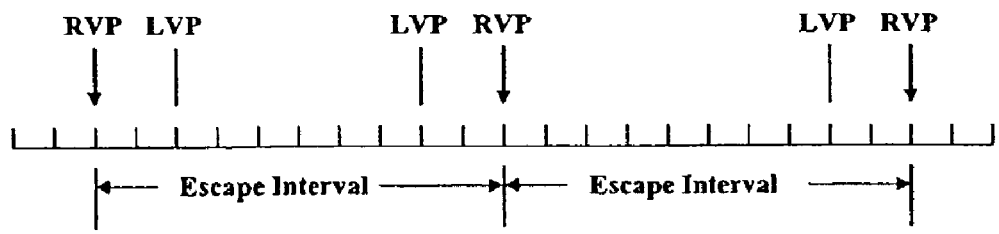
Figure 3D:
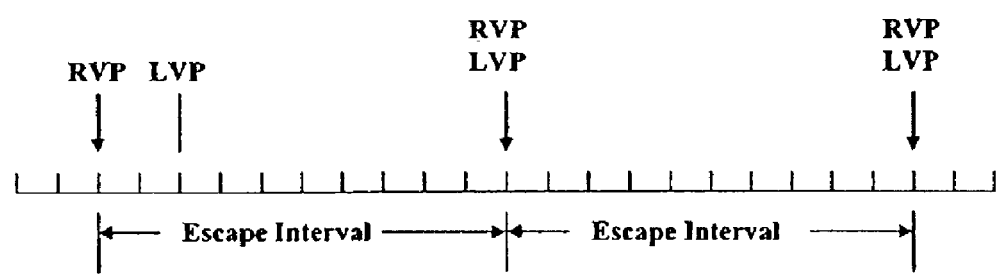
Figure 3E:
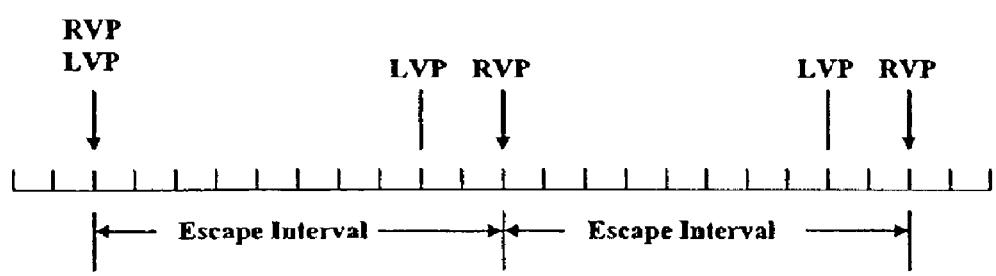

FIGS. 3A through 3E are timing diagrams showing the sequence of right and left ventricular paces (designated as RVP and LVP, respectively) during mode transitions in which the left ventricle may be paced prematurely. The pace delivered upon expiration of the escape interval is designated by an arrow. FIG. 3A shows the timing of left and right ventricular paces when a pacemaker switches from a left ventricular-only pacing mode to a biventricular mode with a negative left ventricular offset interval. FIG. 3B shows the transition from a biventricular pacing mode with a positive left ventricular offset interval to a left ventricular-only mode, and FIG. 3C shows the transition from a biventricular mode with a positive left ventricular offset interval to a biventricular mode with a negative left ventricular offset interval. FIG. 3D illustrates the transition from a biventricular mode with a positive left ventricular offset to a biventricular mode with no offset, and FIG. 3E shows the transition from a biventricular mode with no offset to a biventricular mode with a negative left ventricular offset. In all of these cases, the pacing instant for the left ventricle occurs at an interval shorter than the programmed escape interval during the cardiac cycle in which the mode transition takes place The present invention provides a mechanism for avoiding short-interval paces during mode transitions such as described above. In synchronized pacing modes, one heart chamber or site is paced through a rate sensing/pacing channel and another site is paced through a synchronized sensing/pacing channel with the pacing mode being based upon senses and paces in the rate channel. In accordance with the present invention, if a pacing interval for a synchronized pacing site would be below a specified minimum pacing interval value during a pacing mode transition, the pace to the synchronized site is inhibited for the cardiac cycle in which the transition takes place. In another embodiment, the pacing interval is lengthened by delaying the pace to the synchronized site.

In one embodiment of the invention, a minimum pacing interval value is maintained such that if the pacing interval for a pacing site falls below that value during a mode transition, the pacing instant for the site is delayed by an amount necessary to increase the pacing interval to the minimum value. For example, in the examples illustrated by FIGS. 3A through 3E, the left ventricular pacing instant occurs prematurely at a shorter pacing interval than the programmed ventricular escape interval. Accordingly, the left ventricular pace is delayed until the pace occurs at a minimum pacing interval value. The paces to other sites may be left undisturbed or also delayed to preserve a programmed offset interval. The minimum pacing interval value may be made to correspond with other programmable limits on the pacing rate such as the maximum tracking rate MTR, which limits how fast the atria are allowed to trigger ventricular paces in an atrial tracking mode, or the maximum sensor-indicated rate, which limits how much a rate-adaptive sensor may increase the pacing rate. The minimum pacing interval in the case of left ventricular pacing may also be made to correspond to the left ventricular protective period described above. Alternatively, the minimum pacing interval may be the maximum among a selected number of any other programmable pacing rate limits or may be a parameter separately specified by the user without regard to other programmable limits on the pacing rate.

In another embodiment, if a left ventricular pacing instant occurs at an interval shorter than the minimum pacing interval, the left ventricular pace site is inhibited. When a pacemaker transitions to a left ventricular-only pacing mode from a biventricular mode with a positive offset interval as illustrated in FIG. 3B, this embodiment may cause no pace at all to be delivered during the cardiac cycle in which the transition occurs, similar to the situation when a left ventricular pace is inhibited by a left ventricular sense in a left ventricle-only synchronized pacing mode. To avoid this no pace condition, a right ventricular pace may be delivered when the left ventricular pace is inhibited by the maximum pacing interval, referred to as a right ventricular safety pace.

The examples above have dealt with biventricular pacing modes that are based upon right ventricular events. It should be appreciated that the invention could equally as well be applied to biventricular pacing modes based upon left ventricular events, biatrial pacing, and to multi-site pacing modes.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device, comprising:

pacing a synchronized pacing site in accordance with a first pacing mode in which the synchronized site is paced at a specified pacing instant defined with respect to expiration of an escape interval which is reset by senses or paces occurring at a rate site;

transitioning to a second pacing mode in which the synchronized site is paced at an earlier specified pacing instant defined with respect to expiration of an escape interval than in the first pacing mode; and, inhibiting a pace to the synchronized site at the specified pacing instant during a cardiac cycle in which the transition occurs if the pacing instant occurs at an interval with respect to the previous pacing instant such that the synchronized site would be paced at a rate greater than a programmable maximum pacing rate that limits the pacing rate for the rate and synchronized sites.

2. The method of claim 1 further comprising delivering a delayed pace to the synchronized site during a cardiac cycle where the pace to the synchronized site is inhibited.

3. The method of claim 1 wherein the programmable maximum pacing rate is a maximum sensor-indicated rate.

4. The method of claim 1 wherein the programmable maximum pacing rate is a maximum atrial tracking rate.

5. The method of claim 1 wherein the synchronized site is in the left ventricle and the rate site is in the right ventricle such that and left ventricular paces are delivered upon expiration of a ventricular escape interval based upon right ventricular events.

6. The method of claim 5 wherein either the first or second pacing mode is a biventricular pacing mode with a left ventricular offset.

7. The method of claim 5 wherein the first pacing mode is a biventricular pacing mode with a positive left ventricular offset interval, and the second pacing mode is a left ventricular-only pacing mode.

8. The method of claim 7 wherein a right ventricular safety pace is delivered if the left ventricular pace is inhibited.

9. The method of claim 5 wherein the first pacing mode is a left ventricular-only pacing mode, and the second pacing mode is a biventricular pacing mode with a negative left ventricular offset interval.

10. The method of claim 5 wherein the first pacing mode is a biventricular pacing mode with a positive left ventricular offset interval, and the second pacing mode is a biventricular pacing mode with a negative left ventricular offset interval.

11. The method of claim 5 wherein the first pacing mode is a biventricular pacing mode with a positive left ventricular offset interval, and the second pacing mode is a biventricular pacing mode with no left ventricular offset interval.

12. The method of claim 5 wherein the first pacing mode is a biventricular pacing mode with no left ventricular offset interval, and the second pacing mode is a biventricular pacing mode with a negative left ventricular offset interval.

13. A cardiac rhythm management device, comprising:

sensing/pacing channels for sensing and pacing a plurality of sites;

a controller for controlling the delivery of paces to a pacing site in accordance with a programmed pacing mode, wherein the controller is programmed to:

pace a selected site designated as a synchronized site in accordance with a first pacing mode in which the synchronized site is paced at a specified pacing instant defined with respect to expiration of an escape interval which is reset by a sense or pace occurring at another site designated as the rate site;

transition to a second pacing mode in which the synchronized site is paced at an earlier specified pacing instant defined with respect to expiration of an escape interval than in the first pacing mode; and, inhibit a pace to the synchronized site at the specified pacing instant during a cardiac cycle in which the transition occurs if the pacing instant occurs at an interval with respect to the previous pacing instant such that the synchronized site would be paced at a rate greater than a programmable maximum pacing rate that limits the pacing rate for the rate and synchronized sites.

14. The device of claim 13 wherein the pace to the synchronized site is delayed during a cardiac cycle where the pace to the synchronized site is inhibited.

15. The device of claim 14 wherein the programmable maximum pacing rate is a maximum sensor-indicated rate.

16. The device of claim 13 wherein the programmable maximum pacing rate is a maximum atrial tracking rate.

17. The device of claim 13 wherein the synchronized site is in the left ventricle and the rate site is in the right ventricle such that and left ventricular paces are delivered upon expiration of a ventricular escape interval based upon right ventricular events.

18. The device of claim 17 wherein the first pacing mode is a biventricular pacing mode with a positive left ventricular offset interval, and the second pacing mode is a left ventricular-only pacing mode.

19. The device of claim 18 wherein the controller is programmed to deliver a right ventricular safety pace if the left ventricular pace is inhibited.

20. The device of claim 13 wherein either the first or second pacing mode is a biventricular pacing mode with a left ventricular offset.

* * * * *

UNITED STATES PATENT AND TRADEMARK OFFICE
CERTIFICATE OF CORRECTION

PATENT NO. : 7,142,914 B2  Page 1 of 1
APPLICATION NO. : 10/222130
DATED : November 28, 2006
INVENTOR(S) : Stahmann et al.

It is certified that error appears in the above-identified patent and that said Letters Patent is hereby corrected as shown below:

On the face page, in field (75), in "Inventors", in column 1, lines 2–3, delete "White Bear Lake, MN (US);" and insert -- Overijse (BE); --, therefor.

On the face page, in field (56), Under "Other Publications", in column 2, line 9, delete "2002" and insert -- 2000 --, therefor.

On the face page, in field (56), under "Other Publications", in column 2, line 14, delete "Defribrillator" and insert -- Defibrillator --, therefor.

On the face page, in field (56), under "Other Publications", in column 2, line 17, delete "Defribrillator" and insert -- Defibrillator --, therefor.

On the face page, in field (56), under "Other Publications", in column 2, lines 20–21, delete "Defribrillators" and insert -- Defibrillators --, therefor.

Signed and Sealed this

First Day of May, 2007

JON W. DUDAS
*Director of the United States Patent and Trademark Office*